(12) United States Patent
Cavalier et al.

(10) Patent No.: US 7,892,576 B2
(45) Date of Patent: Feb. 22, 2011

(54) TABLETS COMPRISING A BIOLOGICALLY ACTIVE SUBSTANCE AND AN EXCIPIENT CONTAINING CALCIUM CARBONATE

(75) Inventors: Karine Cavalier, Arles (FR); Didier Sy, Salin de Giraud (FR); Roberto Rosa, Ranco (IT); Bernard Bataille, Saint Gely du Fesc (FR); Michele Delalonde, Saint Gely du Fesc (FR); Gilles Baylac, Jacou (FR); Alberto Galasco, Ferno (IT)

(73) Assignee: Solvay (Societe Anonyme), Brussels (BE)

( * ) Notice: Subject to any disclaimer, the term of this patent is extended or adjusted under 35 U.S.C. 154(b) by 551 days.

(21) Appl. No.: 11/816,326

(22) PCT Filed: Feb. 13, 2006

(86) PCT No.: PCT/EP2006/050886

§ 371 (c)(1),
(2), (4) Date: Dec. 12, 2007

(87) PCT Pub. No.: WO2006/087312

PCT Pub. Date: Aug. 24, 2006

(65) Prior Publication Data
US 2008/0131506 A1 Jun. 5, 2008

(30) Foreign Application Priority Data
Feb. 16, 2005 (FR) .................................. 05 01580

(51) Int. Cl.
*A61K 9/20* (2006.01)
*A61K 47/04* (2006.01)

(52) U.S. Cl. ........................................ 424/465; 514/769
(58) Field of Classification Search ................. 424/465; 514/769
See application file for complete search history.

(56) References Cited

U.S. PATENT DOCUMENTS 2,789,938 A * 4/1957 Wilcox et al. ............... 514/562
3,475,419 A * 10/1969 Miller .......................... 540/32

(Continued)

FOREIGN PATENT DOCUMENTS

CA 2241781 1/1997

(Continued)

OTHER PUBLICATIONS

U.S. Appl. No. 11/995,885, filed Jul. 17, 2006, Lefevre, et al.

(Continued)

*Primary Examiner*—Robert A Wax
*Assistant Examiner*—Aradhana Sasan
(74) *Attorney, Agent, or Firm*—Oblon, Spivak, McClelland, Maier & Neustadt, L.L.P.

(57) ABSTRACT

Tablet comprising at least one biologically active substance and an excipient, in which the excipient contains calcium carbonate and at least one additive selected from fatty acids, their salts, their esters, lipid materials, polysaccharides, polyvinylpyrrolidone and polyvinylpyrrolidone derivatives, acrylic compounds, mono-, di- or triglyceride esters, animal proteins, and mixtures of at least two of these. Method for producing these tablets. Use of calcium carbonate in tablets containing at least one biologically active substance, for the prolonged release of this substance.

11 Claims, 1 Drawing Sheet

U.S. PATENT DOCUMENTS

Figure 1:
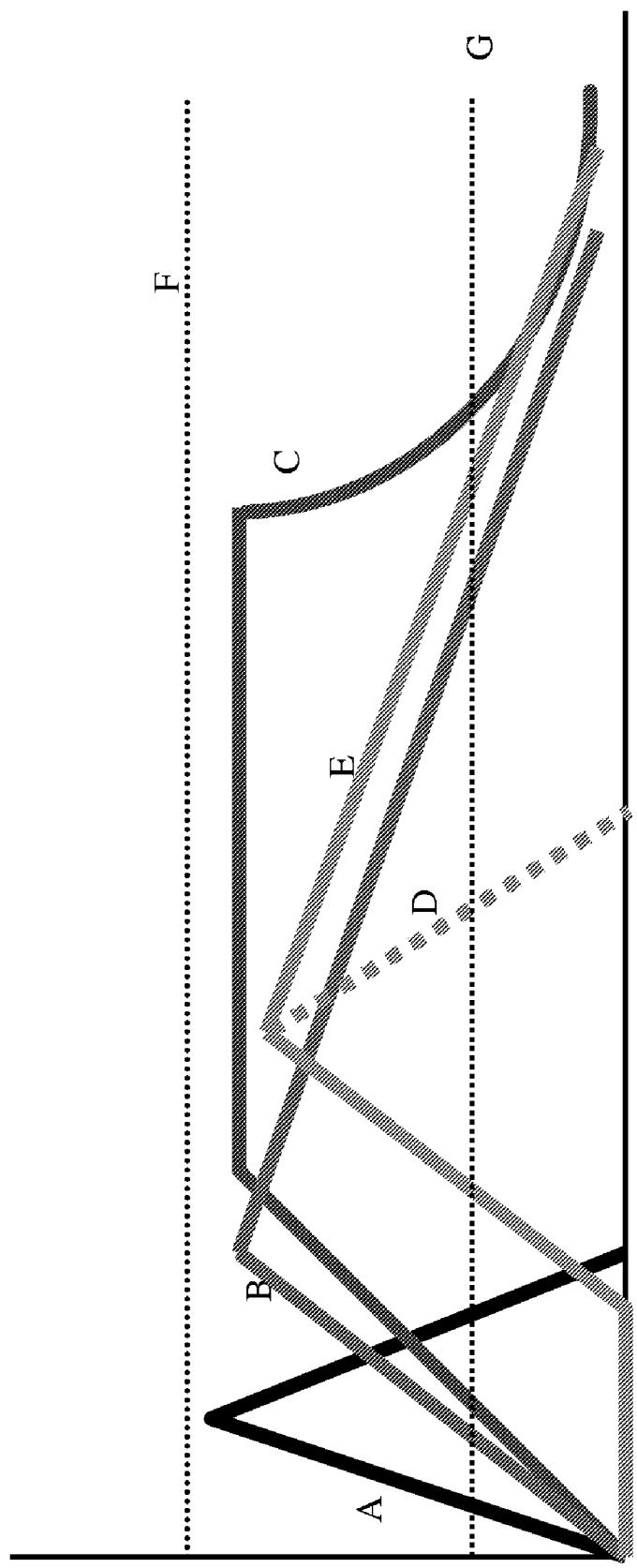

| | | | |
|---|---|---|---|
| 3,597,420 A * | 8/1971 | Archer | 546/202 |
| 4,744,987 A | 5/1988 | Mehra et al. | |
| 5,741,471 A | 4/1998 | Deutsch et al. | |
| 2003/0180208 A1 | 9/2003 | Yaniv | |
| 2003/0211155 A1 | 11/2003 | Makino et al. | |
| 2004/0166047 A1 | 8/2004 | Vogels et al. | |
| 2007/0142527 A1 | 6/2007 | Rosa et al. | |

FOREIGN PATENT DOCUMENTS

| | | |
|---|---|---|
| EP | 0 423 748 | 4/1991 |
| EP | 0 514 711 | 11/1992 |
| EP | 1 380 308 | 1/2004 |
| EP | 1 398 025 | 3/2004 |
| JP | 5-65368 | 3/1993 |
| WO | WO 2006/045768 | 5/2006 |
| WO | WO 2006/051087 | 5/2006 |
| WO | WO 2006/067144 | 6/2006 |
| WO | WO 2006/134080 | 12/2006 |
| WO | WO 2007/009971 | 1/2007 |
| WO | WO 2007/014878 | 2/2007 |
| WO | WO 2007/039625 | 4/2007 |

OTHER PUBLICATIONS

U.S. Appl. No. 12/089,130, filed Oct. 4, 2006, Lefevre, et al.
U.S. Appl. No. 11/719,154, filed May 11, 2007, Cavalier, et al.
U.S. Appl. No. 11/722,269, filed Jun. 20, 2007, Cavalier, et al.
U.S. Appl. No. 11/666,090, filed Apr. 24, 2007, Ricaud, et al.
H. Fausett et al., "Evaluation of Quick Disintegrating Calcium Carbonate Tablets," AAPS Pharmscitech, 2000, Article No. 20, vol. 1., No. 3 XP002349386.
Test Entitled, "Tablet Breaking Strength," European Pharmacopoeia, $5^{th}$ Edition, Chapter 2.9.8., Jan. 2005, cited on p. 9, 1.1-2 of the specification; French version of the $5^{th}$ Edition.
Test Entitled "Dissolution Test for Solid Forms," European Pharmacopoeia, $5^{th}$ Edition, Chapter 2.9.3, p. 242, Jan. 2005, cited on p. 9, 1. 3032 of the sepcification.

* cited by examiner

TABLETS COMPRISING A BIOLOGICALLY ACTIVE SUBSTANCE AND AN EXCIPIENT CONTAINING CALCIUM CARBONATE

CROSS-REFERENCE TO RELATED APPLICATIONS

The present application is a 35 U.S.C. §371 National Stage patent application of International patent application PCT/EP06/050886, filed on Feb. 13, 2006, which claims priority to French patent application FR 0501580, filed on Feb. 16, 2005. International patent application PCT/EP06/050886 and French patent application FR 0501580 are hereby incorporated by reference in their entirety.

The invention relates to tablets comprising at least one biologically active substance and an excipient.

It relates more particularly to tablets where the excipient contains calcium carbonate, to a method for obtaining such tablets and to the use of calcium carbonate in tablets for ensuring prolonged release of the biologically active substance.

The tablet constitutes the form that is most commonly used, most comfortable and most well-accepted by patients for the oral administration of a biologically active substance. Patent application CA 2,241,781 describes tablets for oral administration. Tablets generally comprise the biologically active substance (active ingredient) and an excipient, i.e. a neutral (non-biologically active) system. The latter serves to make the active ingredient easy to absorb and it may also influence the release profile of the active ingredient in the organism. FIG. 1 represents five different theoretical release profiles for oral administration forms. The plasma concentration of the active ingredient (y-axis) is reported as a function of time (x-axis), from the moment of administration. The effective therapeutic window of the active ingredient (window of effective plasma concentration of the active ingredient) is represented by the zone located between lines F and G. Curve A represents a conventional release, rapid release followed by elimination, also rapid, of the active ingredient. Curve B represents a prolonged release of the "sustained release" type, during which the therapeutic level is reached more slowly than for the preceding case, but where this level is maintained for a longer period of time before the gradual elimination of the active ingredient according to a slower rate. This profile corresponds to tablets that are film-coated with a coating of cellulose-based or acrylic derivative type. Curve C represents a prolonged release of the "controlled release" type, during which the therapeutic level is reached more slowly than in the first case, the plasma concentration of the active ingredient reaching a plateau and being maintained for a longer period of time at the level of the plateau (kinetics close to zero order) further to a gradual elimination. This profile corresponds to tablets having a hydrophilic, lipid or insoluble matrix. Curves D and E represent a delayed release of gastroresistant type, characterized by zero release for a certain period of time, followed either by a rapid release (curve D) or by a slow release (curve E). These forms correspondent to tablets that are film coated with a coating of cellulose-based or acrylic derivative type. The excipients most commonly used today are based on polymeric-type organic matrices, such as, for example, hydroxypropylmethylcellulose. The use of such polymeric compounds as an excipient for tablets may constitute a psychological block to their use by patients, who are not naturally very inclined to ingest polymers.

Surprisingly, the applicant has discovered that the organic compounds that go into making up the composition of excipients to tablets could be substantially replaced with calcium carbonate while at the same time conserving the prolonged-release profile of the active ingredient.

The invention is therefore directed towards providing tablets comprising at least one biologically active substance and an excipient, in which the excipient contains calcium carbonate and at least one additive selected from fatty acids, their salts, their esters, lipid materials, polysaccharides, polyvinylpyrrolidones and polyvinylpyrrolidone derivatives, acrylic compounds, mono-, di- or triglyceride esters, animal proteins, and mixtures of at least two of these.

The invention is also directed towards providing a method for obtaining such tablets.

Finally the invention is directed towards the use of calcium carbonate in tablets containing at least one biologically active substance, for the prolonged release of this substance.

The term "tablets" is intended to denote any form made of compressed powder, it being possible for the powder to be agglomerate. The tablets may be of any form, such as the form of pastilles or of lozenges, to mention just a few.

The term "biologically active substance" is intended to denote both substances with a pharmaceutical effect and nutrients, other than calcium carbonate. The biological substance according to the invention can be used in any solid form. It is preferably used in powdered form or in the form of granules. The average size of the particles constituting the biologically active substance is usually greater than or equal to 0.01 µm, more particularly greater than or equal to 1 µm, and most particularly greater than or equal to 10 µm. The size is generally less than or equal to 1000 µm, preferably less than or equal to 800 µm and more particularly preferably less than or equal to 750 µm.

The term "excipient" is intended to denote all the components of the tablet other than the biologically active substance.

The calcium carbonate may be a natural or synthetic calcium carbonate. The natural calcium carbonate may be natural aragonite or calcite, chalk or marble. It may be pre-milled dry or in suspension. Synthetic calcium carbonate is preferred.

The synthetic calcium carbonate can be obtained via any means. Considered among said means are the precipitation of calcium carbonate starting from milk of lime with carbon dioxide (carbonation process) or starting from milk of lime by the addition of an alkaline carbonate (causticisation process) or starting from solutions containing soluble salts of calcium by the addition of an alkaline carbonate.

According to a preferred means in the context of the invention, the precipitated calcium carbonate is obtained by carbonation of a milk of lime. A suspension of precipitated calcium carbonate is thus obtained.

According to a means that is particularly preferred in the context of the invention, calcium carbonate is precipitated by carbonation of a milk of lime with a gas containing carbon dioxide. In this preferred means, the milk of lime is generally obtained by a dispersion of fine particles of quicklime in water, and the gas containing carbon dioxide is advantageously a rich gas, particularly a lime kiln gas.

The calcium carbonate thus precipitated can be optionally isolated from the preparation medium by any known technique, such as filtration, atomization or centrifugation. Filtration and centrifugation techniques are preferred. The calcium carbonate thus obtained may be in the form of a wet cake or of a dry powder.

The term "wet cake" is intended to mean a solid with a water content which is usually greater than or equal to 10%, preferably greater than or equal to 30%. This water content is normally less than or equal to 80% by weight, more specifically less than or equal to 60% by weight and most specifically less than or equal to 50% by weight.

The term "dry powder" is intended to denote a solid whose water content is generally less than or equal to 10% by weight. This content is preferably less than or equal to 5% by weight, and most particularly less than 2% by weight.

The calcium carbonate may be substantially amorphous or substantially crystalline. The term "substantially amorphous or crystalline" is intended to mean that more 50%, in particular more than 75% and preferably more than 90% by weight of the calcium carbonate is in the form of amorphous or crystalline material when analyzed by the X-ray diffraction technique. Substantially crystalline calcium carbonates are preferred. The calcium carbonate may consist of calcite, of vaterite or of aragonite or of a mixture of at least two of these crystallographic varieties. The calcite variety is preferred.

The calcium carbonate occurs as particles. By particles, one intends to denote crystallites or elemental particles and clusters of elemental particles. Crystallites or elemental particles are defined as the smallest discrete particles that can be seen by Electron Microscopy analysis.

The average or mean diameter $d_P$ of the elemental particles of synthetic and natural calcium carbonate can vary to a large extent. This diameter is, however, generally less than or equal to 66 μm, preferably less than or equal to 30 μm, more preferably less than or equal to 10 μm. Particles with a diameter of less than or equal to 1000 nm are especially advantageous, diameters of less than or equal to 500 nm being preferred. Particles with a diameter of greater or equal to 10 nm, preferably of greater or equal to 30 nm, more preferably of greater or equal to 50 nm, yet more preferably of greater than or equal to 70 nm are very suitable. Particles with a diameter of greater than or equal to 100 nm are most particularly suitable. The average diameter of the elemental particles is measured by the Lea and Nurse method, according to standard NF 11601/11602. More specifically, the mean elemental particles diameter $d_P$ is measured by the Lea and Nurse method (Standard NFX 11-601, 1974). The $d_P$ value is obtained from the massic area ($S_M$) derived from the Lea and Nurse method by making the assumptions that all the particles are spherical, non porous and of equal diameter, and by neglecting contact surfaces between the particles.

The relationship between $d_P$ and $S_M$ is the following:

$$d_P = 6/(\rho S_M)$$

where

ρ is the specific mass of the calcium carbonate.

The size distribution of the calcium carbonate particles involved in the tablets according to the invention is obtained from sedimentation methods using a Micromeritics Sedi-Graph 5 100 measuring device for sizes ranging from 0.1 to 300 μm (standard ISO 13317-3) and using a Horiba CAPA 700 measuring device for sizes ranging from 0.01 to 300 μm (standard ISO 13318-2). The mean size of the particles (equal to the value of $D_{50}$ defined below) is commonly higher than or equal to 0.030 μm, often higher than or equal to 0.050 μm, frequently higher than or equal to 0.070 μm, specifically higher than or equal to 0.100 μm and most specifically higher than or equal to 0.150 μm. The mean size of the particles is generally lower than or equal to 66 μm, frequently lower than or equal to 20 μm, more frequently lower than or equal to 10 μm, often lower than or equal to 5 μm, specifically lower than or equal to 3 μm and most specifically lower than or equal to 2 μm. $D_{50}$ is the particle size value which expresses that 50% by vol of the particles have a size value lower than or equal to $D_{50}$.

The calcium carbonate involved in the tablets according to the invention generally has a BET specific surface area of greater than or equal to 0.1 $m^2/g$, preferably greater than or equal to 1 $m^2/g$. The specific surface area is advantageously greater than or equal to 3 $m^2/g$. A specific surface area of greater than or equal to 5 $m^2/g$ is particularly recommended. The specific surface area is generally less than or equal to 100 $m^2/g$, preferably less than or equal to 70 $m^2/g$, specific surface area values of less than or equal to 50 $m^2/g$ being most particularly preferred. The BET specific surface area is measured according to the standard ISO 9277-1995.

The calcium carbonate involved in the tablets according to the invention can exhibit various morphologies. The particles can have the form of needles, scalenohedra, rhombohedra, spheres, platelets or prisms. These forms are determined by means of electron microscopy techniques. The scalenohedra and rhombohedra forms are preferred.

The calcium carbonate according to the invention may optionally be premixed with the additive.

When the additive is chosen from fatty acids, the latter may be saturated or unsaturated, and substituted or unsubstituted. They comprise a carbon atom number generally greater than or equal to 6, preferably greater than or equal to 12, and most particularly greater than or equal to 14. This carbon atom number is usually less than or equal to 28, and more particularly less than or equal to 22. A carbon atom number of less than or equal to 18 is particularly suitable.

When the additive is chosen from lipid materials, the latter comprise compounds chosen from waxes, animal fats, plant fats, mineral oils, animal oil and plant oils. The plant oils include, but are not limited to, canola oil, coconut oil, cottonseed oil, rapeseed oil, sunflower seed oil, palm oil and soothing oil.

When the additive is chosen from polysaccharides, the latter comprise compounds chosen from plant gums, cellulose and cellulose derivatives, natural starches and substituted or hydrolyzed starch derivatives.

When the additive is chosen from plant gums, the latter include, but are not limited to, alginates, carraghenate, furcellaran, pectin, agar gum, carob gum, ghatti gum, guar gum, gum tragacanth, acacia gum, gum Arabic, xanthan gum, karaya gum and tara gum.

When the additive is chosen from cellulose derivatives, the latter include, but are not limited to, hydroxypropylmethylcellulose, hydroxypropylcellulose, hydroxypropylethylcellulose and ethylcellulose.

When the additive is chosen from substituted or hydrolyzed starch derivatives, the latter include, but are not limited to, dextrin, maltodextrin and cyclodextrines.

When the additive is chosen from acrylic compounds, the latter comprise compounds such as acrylic acid ethers, and in particular methacrylates.

When the additive is chosen from animal proteins, the latter comprise in particular gelatine.

The additive content of the calcium carbonate is generally greater than or equal to 0.1 wt % of the calcium carbonate, preferably greater than or equal to 0.5 wt %, and most particularly greater than or equal to 1.0 wt %. The content is usually less than or equal to 30 wt % of the calcium carbonate, and more particularly less than or equal to 20 wt %. A content of less than or equal to 15 wt % is particularly suitable.

The calcium carbonate involved in the tablets according to the invention can be used in any solid form. It is preferred to use it in the form of powder, of granules or any mixture thereof. The term "powder" is intended to denote a state where more than 95% by weight of the particles have a size measured by sieving which is lower than 66 μm. For powders, the average size of the particles measured by the Lea and Nurse method is usually greater than or equal to 0.010 μm, more particularly greater than or equal to 0.030 μm, and most particularly greater than or equal to 0.050 μm. This size is generally less than or equal to 66 μm, preferably less than or equal to 10 μm, more preferably less than or equal to 1 μm, and most particularly preferably less than or equal to 0.5 μm. The term "granules" is intended to denote a state where more than 95% by weight of the particles have a size measured by sieving which is higher than or equal to 66 μm. The average size of the granules measured by the sieving method is usually greater than or equal to 66 μm, more particularly greater than or equal to 100 μm, and most particularly greater than or equal to 150 μm. This size is generally less than or equal to 2000 μm, preferably less than or equal to 1000 μm, and more particularly preferably less than or equal to 800 μm.

The calcium carbonate granules can be obtained starting from powder by any granulation method. These methods may be wet granulation (conventional granulation, spheronization, extrusion, atomization, etc.) or dry granulation (compacting and briquetting). These methods generally use binders. Among the latter, mention may be made of polyvinylpyrrolidone, gum Arabic, starch, maltodextrin, etc. The amount of binder is generally greater than or equal to 2% and less than or equal to 10% by weight of the granules.

The additives of the calcium carbonate can optionally be added at any stage in the production of the calcium carbonate, i.e. added to the suspension of calcium carbonate, to the wet cake or to the dry powder, and/or during the granulation and/or during the production of the tablets.

These additives are found at least partially in the tablets.

The calcium carbonate content in the excipient is generally greater than or equal to 20% by weight, preferably greater than or equal to 50% by weight, more particularly greater than or equal to 65% by weight, still more preferably greater than or equal to 70% by weight, yet more preferably greater than 76% by weight, most preferably greater than or equal to 85% by weight and in particular greater than or equal to 90% by weight. A content of greater than or equal to 95% by weight and preferably of greater than or equal to 98% by weight is particularly suitable.

The excipient content in the tablet is generally greater than or equal to 10% by weight, preferably greater than or equal to 20% by weight, and most particularly greater than 30 wt %. The excipient content in the tablet is generally less than or equal to 90% by weight, preferably less than or equal to 80% by weight, and most particularly less than 70 wt %.

The calcium carbonate content in the tablet is generally greater than or equal to 2% by weight, preferably greater than or equal to 10% by weight, more particularly greater than or equal to 30% by weight, and most particularly greater than or equal to 70% by weight. A content of greater than or equal to 85% by weight is particularly suitable. The calcium carbonate content in the tablet is generally lower than or equal to 90% by weight.

The invention also relates to a method for producing tablets. The tablets according to the invention can be obtained by various methods.

In general, the tablets are obtained by compression of a mixture comprising at least one biologically active substance, calcium carbonate, at least one additive and, optionally, at least one binder and/or at least one lubricant.

Preferably, the tablets are obtained by compression of a mixture comprising the biologically active substance, the calcium carbonate and the additive, in the form of powders or of granules or of mixtures thereof.

According to a first embodiment, the tablets are obtained by compression of a mixture comprising the biologically active substance, the calcium carbonate mixed with the additive in the form of powders and, optionally, at least one binder and/or at least one lubricant. The amount of binder is generally greater than or equal to 2 and less than or equal to 10% by weight of tablet. The amount of lubricant is usually greater than or equal to 0.01 and less than or equal to 2% by weight of tablet.

According to a second embodiment which is preferred, the tablets are obtained by compression of granules optionally in the presence of a lubricant.

According to a first variant of the second embodiment, a mixture of powders of calcium carbonate mixed with the additive, of the active ingredient and of a binder is prepared in a first step. This mixture is then subjected to a granulation process. The granules obtained are then mixed with a lubricant and then compressed so as to obtain tablets.

According to a second variant of the second embodiment, a mixture of calcium carbonate mixed with the additive and, optionally, a binder is prepared in a first step. This mixture is then subjected to a granulation process. The granules obtained are then mixed with granules of the active ingredient and optionally with a lubricant, and the mixture thus obtained is then compressed so as to obtain tablets.

Methods and equipment of any type intended for the granulation of powders can be used for the production of the granules. The granulation can, for example, be carried out in a device of compactor type (AlexanderWerk, Bepex), in atomizers, in fluidized beds, etc. The granulation conditions are adjusted so as to obtain granules as defined above.

Methods and equipment of any type intended for the compression of powders or of granules can be used. The compression duration and pressure are adjusted so as to obtain tablets of sufficient hardness. The hardness is measured by the method described in the test entitled "Tablet breaking strength", No. 2.9.8., European Pharmacopoeia, $5^{th}$ Edition (January/2005: 20908).

The invention also relates to the use of calcium carbonate in tablets containing at least one biologically active substance, for the prolonged release of this substance.

More specifically, the invention relates to the use of calcium carbonate and of at least one additive selected from fatty acids, their salts, their esters, lipid materials, polysaccharides, polyvinylpyrrolidone and polyvinylpyrrolidone derivatives, acrylic compounds, mono-, di- or triglyceride esters, animal proteins, and mixtures of at least two of these, in tablets containing at least one biologically active substance, for the prolonged release of this substance.

Still more specifically, the invention relates to the use of calcium carbonate and of at least one additive, in tablets containing at least one biologically active substance, for the prolonged release of this substance, the content of calcium carbonate being higher than 76% by weight of the tablet after having subtracted the active ingredient weight from the tablet weight.

These tablets can be used for prolonged release of the active ingredient when they are administered orally.

The term "prolonged release profile" is intended to denote a profile similar to type C of FIG. 1.

The expression "prolonged release of the active ingredient" is intended to mean a release according to slow kinetics so as to ensure a prolonged therapeutic effect, in particular for active ingredients with a short biological half-life. This means that at least 10% and at most 50% of the biologically active substance (active ingredient), preferably at least 20% and at most 40%, is released in the first hour following administration of the tablet, the remaining percentage of the biologically active substance being released over a period of at least 7 hours and at most 24 hours, preferably over a period of at least 7 hours and at most 16 hours. One has simulated the administration of the tablet by carrying out a test according to the procedure described in the European Pharmacopoeia, 5th Edition, January 2005, Chapter 2.9.3., page 242, test entitled "Dissolution test for solid forms". The test was carried out in an Erweka DT 6R-type rotating paddle device described in European Pharmacopoeia. The reactor is closed, and perfectly stirred. The hydrodynamic conditions, the temperature and the duration are fixed and constant, a pH variation is imposed. The tablets (400 mg) are immersed in 900 ml of liquid.

The following examples serve to illustrate the invention without, however, limiting the scope of the claims.

In these examples, theophylline was used as active ingredient in the tablet. The dissolution profile of this active ingredient at 37° C., in an aqueous solution maintained at pH 1.2 for 1 h and then at pH 6.8 for 7 h, was determined. The concentration of the dissolved active ingredient was measured by UV spectrophotometry at a wavelength of 264 nm. The percentage of dissolved (release) active ingredient over time was plotted. The curves obtained are characterized by the slopes of the linear portions corresponding to the beginning (pH 1.2) and to the end (pH 6.8) of the test and by the time required to observe a release of 50% of the active ingredient.

EXAMPLE 1

Preparation of a Precipitated Calcium Carbonate (PCC) Containing at Least One Additive (in Accordance with the Invention)

A stream of carbon dioxide gas containing 22 vol % of $CO_2$ was introduced into a 40 l reactor comprising a milk of lime with a lime concentration (expressed as $CaCO_3$) of 180 .mu.l, at a temperature of 50° C. and at a flow rate of 16 m$^3$/h. After approximately 110 minutes, 100% of the calcium hydroxide has been converted to calcium carbonate. An amount of starch was added to the suspension obtained, so as to obtain, after filtration and drying, a starch content of 4.7% by weight of the calcium carbonate.

EXAMPLE 2

Preparation of a Precipitated Calcium Carbonate (PCC) Containing at Least One Additive (in Accordance with the Invention)

A stream of carbon dioxide gas containing 22 vol % of $CO_2$ was introduced into a 40 l reactor containing a milk of lime with a lime concentration (expressed as $CaCO_3$) of 180 μl, at a temperature of 50° C. and at a flow rate of 16 m$^3$/h. After approximately 110 minutes, 100% of the calcium hydroxide has been converted to calcium carbonate. The suspension obtained was subjected to a filtration process. The calcium carbonate obtained by filtration was dried at approximately 105° C. for 24 h and then milled. An amount of polyvinylpyrrolidone (PVP) was added to the dry PCC so as to obtain a PVP content of 5% by weight of the calcium carbonate, and mixing was carried out at 25° C.

EXAMPLE 3

Preparation of a Precipitated Calcium Carbonate Containing at Least One Additive (in Accordance with the Invention)

A stream of carbon dioxide gas containing 30 vol % of $CO_2$ was introduced into a 40 reactor containing a milk of lime with a lime concentration (expressed as $CaCO_3$) of 180 μl, at a temperature of 20° C. and at a flow rate of 16 m$^3$/h. After approximately 90 minutes, 100% of the calcium hydroxide has been converted to calcium carbonate.

20 of the suspension of PCC obtained was brought into contact with 1 l of an aqueous emulsion containing 1 g of stearin (mixture of steric acid, palmitic acid and oleic acid), with stirring, for 45 minutes at 75° C.

An amount of starch was added to the suspension obtained, so as to obtain, after drying, a starch content of 4.0% by weight of the calcium carbonate. The PCC particles were dried at 105° C. until their water content was less than 3 g/kg, and were then milled. The stearin content of the PCC is thus 2.8 g/kg.

EXAMPLE 4

Preparation of a Precipitated Calcium Carbonate Containing at Least One Additive (in Accordance with the Invention)

The procedure of Example 3 was followed, except that the starch was replaced with PVP so as to obtain a PVP content of 5.0% by weight of the calcium carbonate.

EXAMPLE 5

Preparation of PCC Granules (in Accordance with the Invention)

The powders obtained in Examples 1 to 4 were granulated in a compactor-type device (AlexanderWerk, Bepex). The granules obtained have an average size of between 250 and 700 μm.

EXAMPLE 6

Preparation of Granules Containing the PCC and the Active Ingredient (in Accordance with the Invention)

200 g of PCC powder obtained according to the procedure of Example 2, but where the PVP content is 10% by weight, 200 g of powdered theophylline and 40 g of PVP were mixed in a Turbula-type tumbling mixer and wetted in a Kenwood-type planetary blender. The granulation was carried out by passing the wet mixture through a screen with a calibrated mesh, in an Erweka FGS-type oscillating granulator. The granules were then dried in a fluidized bed at 60° C. in a Glatt TR2 drying device.

EXAMPLES 7 TO 10

Preparation of Tablets Starting from Granules of PCC and Granules of Active Ingredient (in Accordance with the Invention)

200 g of granules of PCC respectively obtained according to one of Examples 1 to 4 were mixed with 200 g of granulated theophylline (BASF, theophylline anhydrous granules 0.2/0.7) and 2 g of magnesium stearate in a Turbula-type tumbling mixer. The mixture was then compressed in a Frogerais OA-type instrument machine, the compression chamber being regulated so as to receive 400 mg of mixture, at an appropriate pressure and for an appropriate period of time so as to obtain a tablet exhibiting a hardness of between 45 and 55 N.

EXAMPLE 11

Preparation of Tablets Starting from Granules Containing the PCC and the Active Ingredient (in Accordance with the Invention)

The procedure of Example 7 was followed, using 400 mg of granules obtained according to Example 6 and 4.5 mg of magnesium stearate.

EXAMPLE 12

Tablets Containing Theophylline and a Hydroxypropylmethylcellulose Matrix-Based Excipient (not in Accordance with the Invention)

It involves a commercial product from the Laboratoire Fabre, Theostat LP 200 mg. The excipient is hydroxypropylmethylcellulose-based and also comprises lactose (diluent), magnesium stearate (lubricant during the compacting step) and colloidal silica (to ensure flowability).

Test for Active Ingredient Release Kinetics

The test was carried out according to the procedure described in the European Pharmacopoeia, 5th Edition, January 2005, Chapter 2.9.3., page 242, test entitled "Dissolution test for solid forms". The test was carried out in an Erweka DT 6R-type rotating paddle device described in European Pharmacopoeia. The reactor is closed, and perfectly stirred. The hydrodynamic conditions, the temperature and the duration are fixed and constant, a pH variation is imposed. The tablets (400 mg) are immersed in 900 ml of liquid.

Hydrodynamic conditions:
Stirring paddle speed 50 rpm
Temperature 37° C.
Test duration: 8 h Procedure 1 (for the Tests on the Tablets Obtained According to Examples 7 to 10 and 12)

pH of 1.2 for 1 h via a solution of HCl and then pH of 6.8 via a phosphate-based buffer solution for the remaining 7 hours.

Regular samples of solution were taken and diluted to 1/50th, and the dissolved active ingredient was assayed by UV spectrophotometry at 264 nm.

The results of the test for active ingredient release kinetics are given in Table 1. The slopes (% of active ingredient dissolved per minute) of the linear portions of the dissolution curves corresponding to the beginning (pH 1.2) and to the end (pH 6.8) of the test, and also the time required to attain 50% dissolution of the active ingredient, are reiterated therein.

Procedure 2 (for the Tests on the Tablets Obtained, Compressed According to Example 11)

pH of 1.5 for 1 h via a solution of HCl and then pH of 4.5 for 2 h and subsequently pH of 7.5 for 5 hours via a buffer solution (56.3% of trishydroxymethylaminomethane and 43.7% of anhydrous sodium acetate).

Regular samples of solution were taken and diluted to 1/50th, and the dissolved active ingredient was assayed by UV spectrophotometry at 264 nm.

The results of the test for active ingredient release kinetics are given in Table 2. The slopes (% of active ingredient dissolved per minute) of the linear portions of the dissolution curves corresponding to the beginning (pH 1.5) and to the end (pH 7.5) of the test, and also the time required to attain 50% dissolution of the active ingredient (AI), are reiterated therein.

TABLE 1

| Example | Slope pH 1.2 (%/min) | Slope pH 6.8 (%/min) | Dissolution time 50% AI (min) |
|---|---|---|---|
| 7 | 0.745 | 0.047 | 70 |
| 8 | 0.881 | 0.047 | 60 |
| 9 | 0.444 | 0.055 | 215 |
| 10 | 0.399 | 0.099 | 185 |
| 12 | 0.120 | 0.120 | 210 |

TABLE 2

| Example | Slope pH 1.5 (%/min) | Slope pH 7.5 (%/min) | Dissolution time 50% AI (min) |
|---|---|---|---|
| 11 | 0.92 | 0.033 | 60 |

The invention claimed is:

1. A prolonged release tablet comprising at least one biologically active substance and an excipient, wherein the excipient comprises:
   greater than or equal to 85% by wt. calcium carbonate, and
   at least one additive selected from the group consisting of lipid materials, polysaccharides, polyvinylpyrrolidone, polyvinylpyrrolidone derivatives, acrylic compounds, animal proteins, and mixtures thereof,
   and wherein said tablet provides prolonged release of the biologically active substance such that at least 10% and at most 50% of the biologically active substance is released in the first hour following oral administration of the tablet, the remaining percentage of the biologically active substance being released over a period of at least 7 hours and at most 24 hours.

2. The tablet according to claim 1, wherein the calcium carbonate is a precipitated calcium carbonate.

3. The tablet according to claim 1, wherein the excipient comprises more than 90 wt. % calcium carbonate.

4. The tablet according to claim 1, wherein the calcium carbonate exhibits at least one of the following characteristics:
   a) the crystallographic phase is calcite;
   b) the BET specific surface area ranges from 0.1 $m^2/g$ to 100 $m^2/g$;
   c) the calcium carbonate exists as particles having a mean diameter $d_p$, as measured by the Lea and Nurse method, ranging from 0.010 µm to 66 µm;
   d) the calcium carbonate exists as particles having a mean size $D_{50}$, as measured by a sedimentation technique, ranging from 0.030 µm to 66 µm; and/or
   e) the calcium carbonate exists as particles having an average size, as measured by sieving, ranging from 66 µm to 2000 µm.

5. The tablet according to claim 1, wherein the additive is selected from the group consisting of:
   a. fatty acids having from 6 to 28 carbon atoms;
   b. lipid materials comprising waxes, animal fats, plant fats, mineral oils, animal oils, and plant oils;

c. polysaccharides comprising plant gums, cellulose, cellulose derivatives, native starches, and substituted or hydrolyzed starch derivatives; and d. acrylic compounds comprising acrylic acid ethers and methacrylates.

6. A method, comprising orally administering the tablet according to claim 1 to a patient.

7. A method for producing one or more tablets according to claim 1, wherein said method comprises compressing a mixture comprising at least one biologically active substance, calcium carbonate, at least one additive, and optionally, at least one binder and/or at least one lubricant.

8. The method according to claim 7, wherein the biologically active substance, the calcium carbonate, and the additive are each independently in the form of powders, granules, or mixtures thereof.

9. The method according to claim 8, wherein said method comprises compressing granules, wherein the granules are either a single type comprising the biologically active substance, the calcium carbonate, and the additive, or two types comprising a first type comprising the biologically active substance, and a second type comprising the calcium carbonate and the additive.

10. The tablet according to claim 1, wherein the at least one additive is selected from the group consisting of fatty acids, salts of fatty acids, esters of fatty acids, monoglyceride esters, diglyceride esters, triglyceride esters, and mixtures thereof.

11. The tablet according to claim 1, wherein at least 20% and at most 40% of the biologically active substance is released in the first hour following oral administration of the tablet, the remaining percentage of the biologically active substance being released over a period of at least 7 hours and at most 16 hours.

* * * * *